United States Patent [19]

Kageyama

[11] Patent Number: 4,914,965

[45] Date of Patent: Apr. 10, 1990

[54] CRACK SHEAR DISPLACEMENT GAGE

[75] Inventor: Kazuo Kageyama, Tsukuba, Japan

[73] Assignee: Agency of Industrial Science & Technology, Ministry of International Trade & Industry, Tokyo, Japan

[21] Appl. No.: 329,935

[22] Filed: Mar. 28, 1989

[30] Foreign Application Priority Data

Mar. 31, 1988 [JP] Japan .................................. 63-80078

[51] Int. Cl.⁴ ............................................ G01N 19/08
[52] U.S. Cl. ........................................ 73/799; 73/842
[58] Field of Search ................. 73/799, 842, 841, 845, 73/851, 150 A, 854, 849

[56] References Cited

FOREIGN PATENT DOCUMENTS 185529 8/1966 U.S.S.R. ............................ 73/150 A
485364 12/1975 U.S.S.R. ............................ 73/150 A

Primary Examiner—Jerry W. Myracle
Attorney, Agent, or Firm—Oblon, Spivak, McClelland, Maier & Neustadt

[57] ABSTRACT

A crack shear displacement gage for use in determining the critical load of a composite laminate by providing the laminate with a crack at one end, applying a load to near the center of the laminate, and measuring the shift in the longitudinal direction between the end portions of the laminate above and below the crack. The gage comprises a frame, a fixing member mounted on the frame and having a head for clamping the end portion of the laminate above the crack, a contact for contacting the end face of the end portion below the crack, a spring member for urging the contact against the end face, and a strain gage mounted on the spring member for detecting the strain of the spring member.

3 Claims, 5 Drawing Sheets

CRACK SHEAR DISPLACEMENT GAGE

BACKGROUND OF THE INVENTION

1. Field of the Invention

This invention relates to a crack shear displacement gage for use in property evaluation testing, quality control and the like of composite laminates.

2. Prior Art Statement

According to one known method for testing the toughness of, for example, a composite laminate, an end-notched flexure specimen of the material is supported at opposite ends in the manner of a beam, a concentrated vertical load is applied thereto, and the relationship between the amount of load and the load line displacement are recorded in the form of a chart. This enables the fracture toughness to be determined from the maximum load.

In the case of a brittle material, the maximum load is substantially the same as the critical load, namely the load at the time that crack growth begins, and can thus be used as an index of the fracture point. In the case of a tough composite laminate, however, it is the critical load that serves as the index of the fracture point. (See FIG. 8.) It is thus very important to be able to detect the critical load with high accuracy.

In the aforesaid test method employing an end-notched flexure specimen, however, it is not possible to determine the critical load from the chart showing the relationship between the load and the load line displacement.

The critical load can, however, be determined with high precision by measuring the "crack shear displacement." In this specification, the term "crack shear displacement (CSD)" is defined to mean the lateral shift occurring at an end of a test specimen between the portions above and below a lateral crack when a test specimen is provided with a lateral crack inwardly from an end face thereof and is then subject to bending.

The conventional displacement gage measures the amount of crack opening in the direction perpendicular to the crack face, making it impossible to determine the critical load from the measured value.

OBJECT AND SUMMARY OF THE INVENTION

The main object of this invention is to provide a crack shear displacement gage which enables the critical load, which constitutes an index of the fracture point, to be determined accurately.

For attaining this object, this invention provides a crack shear displacement gage comprising a frame, a fixing member having one end fixed on the frame and having at the other end a head which can be detachably fixed in a clamping manner on a first end portion of a test specimen whose end portion is divided into first and second end portions by a crack, a contact for contacting an end face of the second end portion of the test specimen, a spring member whose one end is fixed on the frame and whose other end supports the contact for urging the contact against the end face of the second end portion, and a strain gage mounted on the spring member for detecting the strain of the spring member.

In the crack shear displacement gage of this structure, when a load applied to the test specimen causes the first and second end faces to shift with respect to each other along the crack by which they are separated, the contact is displaced as it follows the motion and this displacement appears as strain in the spring member. The strain gage detects the strain to thereby detect the crack shear displacement (CSD) corresponding to the applied load.

The point of intersection between the initial load-CSD line and a secant line whose slope is 5% smaller than the CSD line is the critical load. The critical load can thus be accurately determined by detecting the CSD.

The above and other features of the present invention will become apparent from the following description made with reference to the drawings.

DETAILED DESCRIPTION OF THE PREFERRED EMBODIMENT

Figure 1:
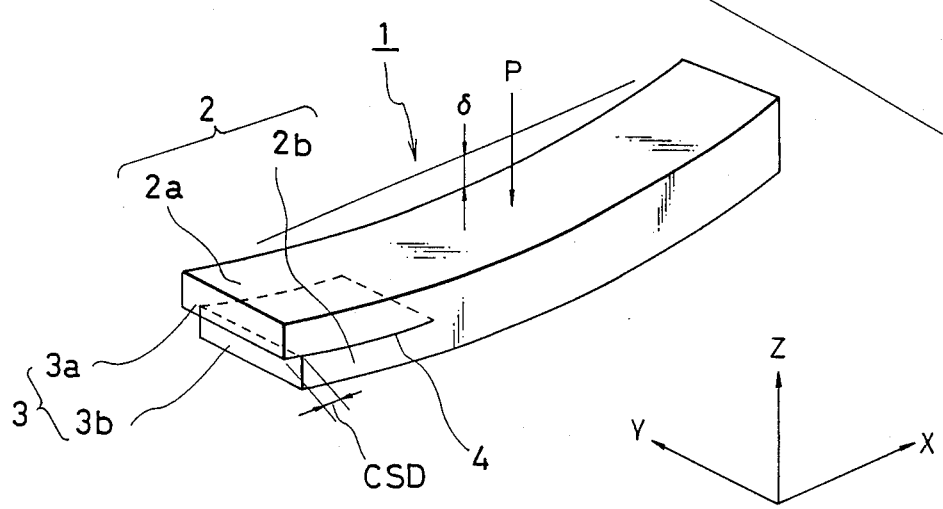
FIG. 1 is a perspective view for explaining a test specimen with which the crack shear displacement gage according to this invention is used.

An explanation will first be given on the test specimen with respect to which the crack shear displacement measurement is carried out. Referring to FIG. 1, a test specimen 1 is a bar-shaped member of square or rectangular cross-section. This test specimen 1 will be discussed with respect to a three-dimensional coordinate system (X, Y, Z), as shown in FIG. 1. A crack 4 is formed to extend from an end face 3 (YZ plane) of the specimen 1 longitudinally (in the direction of the X-axis) into an end portion 2. The crack 4 thus divides the end portion 2 into an upper portion 2a and a lower portion 2b.

The test specimens which can be tested with the crack shear displacement gage according to this invention include both brittle and tough materials. To be specific, there can be cited a carbon-epoxy composite material, a carbon-PEEK composite material, and laminates each consisting of a plurality of layers of the carbon-epoxy composite materials and/or the carbon-PEEK composite materials. When a laminate is used as the test specimen, it can be easily provided with a crack of a desired length by inserting a non-adhesive film of a size equal to the desired length between adjacent layers of composite materials at the time the layers of the laminate are adhered together to form the composite.

Figure 2:
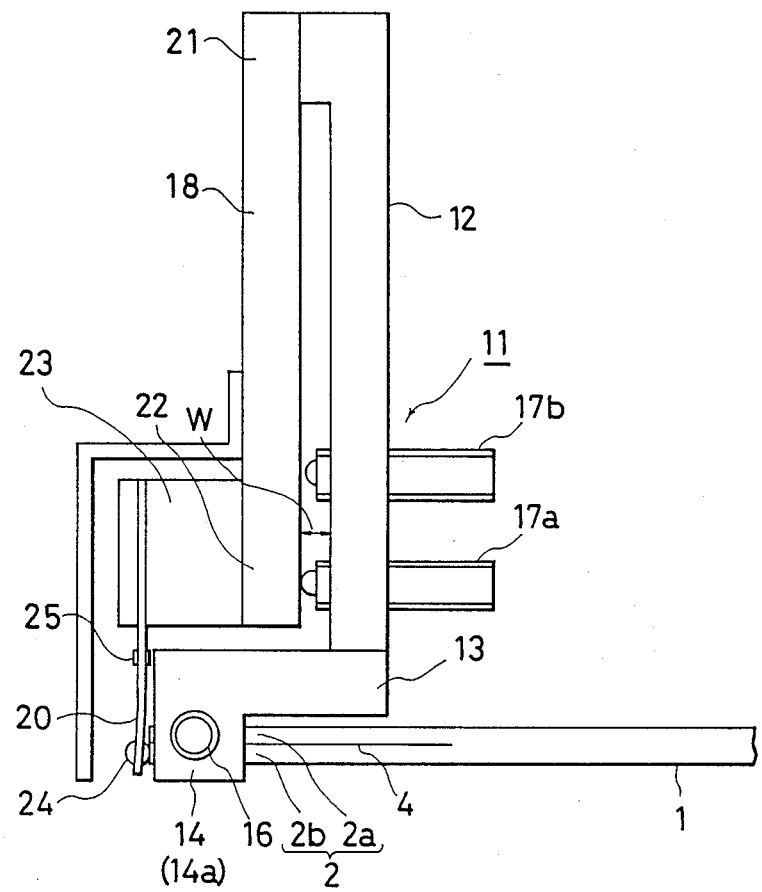
FIG. 2 is a front view of an embodiment of the crack shear displacement gage according to this invention.
Figure 3:
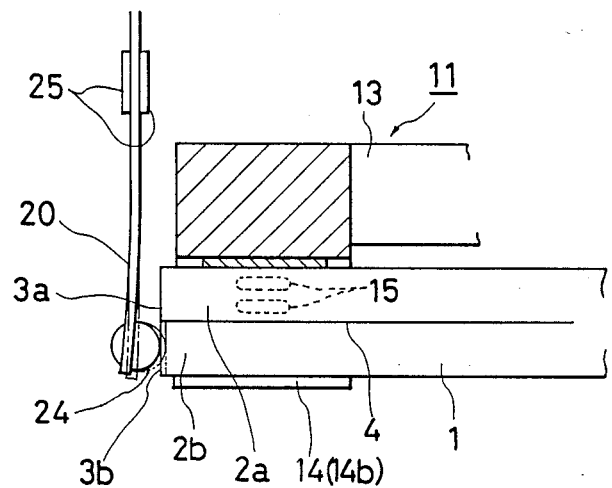
FIG. 3 is an enlarged sectional view of an essential portion of the crack shear displacement gage of FIG. 2.
Figure 4:
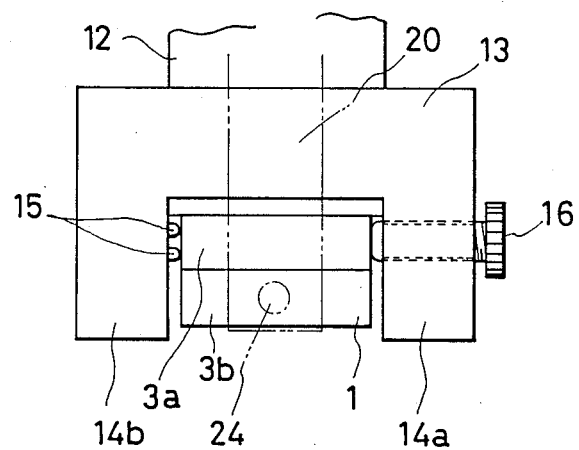
FIG. 4 is a side view showing the fixing head of the crack shear displacement gage of FIG. 2.

FIGS. 2–4 illustrate a crack shear displacement gage 11 which is one embodiment of this invention. The gage 11 has a frame 12 to the bottom end of which is attached a fixing member 13 for fixing in place the test specimen 1. The free end of the fixing member 13 is provided with fixing head 14 constituted as a pair of arms 14a and 14b.

The arm 14a has an internally threaded hole into which a screw 16 is screwed, and the arm 14b has a plurality of projections 15 formed on an inner surface thereof opposed to the threaded hole of the arm 14a. The opposite side surfaces of the upper portion 2a of the end portion 2 of the test specimen 1 are positioned between the arms 14a and 14b and, by the use of the screw 16, the test specimen 1 is retained non-rotatably about the upper portion 2a within the fixing head 14 (FIG. 4).

To the top end of the frame 12 is fixed the base end 21 of a lever holder 18, which is a rod-shaped member with a large spring constant. A pair of screws 17a and 17b are engaged in threaded holes of the frame 12 such that the tip end of the screw 17a abuts on the lever holder 18 in the vicinity of the tip end 22 thereof. The gap W between the tip end 22 of the lever holder 18 and the frame 12 can be adjusted by advancing and retracting the screw 17a. A head 23 provided on the tip end 22 of the lever holder 18 has a cantilever 20 extending downward therefrom. The cantilever 20 is constituted as a narrow and thin plate spring. A contact 24 is provided on the cantilever 20 near its tip end so as to be positioned opposite the end face 3b of the lower portion 2b of the test specimen 1 (FIG. 3). A strain gage 25 is disposed on the cantilever 20 so as to enable detection of the amount of flexing of the cantilever.

The operation of the so-constituted crack shear displacement gage 11 in measuring the crack shear displacement of the test specimen 1 will now be explained.

First the screw 17a on the frame 12 is adjusted to move the lever holder 18 so as to cause the contact 24 of the cantilever 20 to separate from the fixing head 14. Next, the end portion 2 of the specimen 1 is inserted between the arms 14a and 14b of the fixing head 14, and the screw 16 on the arm 14a is adjusted so as to clamp the upper portion 2a of the test specimen 1 between the screw 16 and the projections 15, thereby fixing it on the fixing head 14 of the fixing member 13.

The screw 17a is then turned slowly in the direction which causes the lever holder 18 to approach the frame 12, thereby causing the contact 24 of the cantilever 20 to come in contact with the end face 3b of the lower portion 2b of the test specimen 1. After contact has been made, the screw 17a is further turned in the same direction while observing the strain gage 25 provided on the cantilever 20. When the reading on the strain gage reaches a prescribed value, turning of the screw 17a is discontinued. The screw 17b acts as a stop for preventing the lever holder 18 from coming too close to the frame 12.

Figure 5:
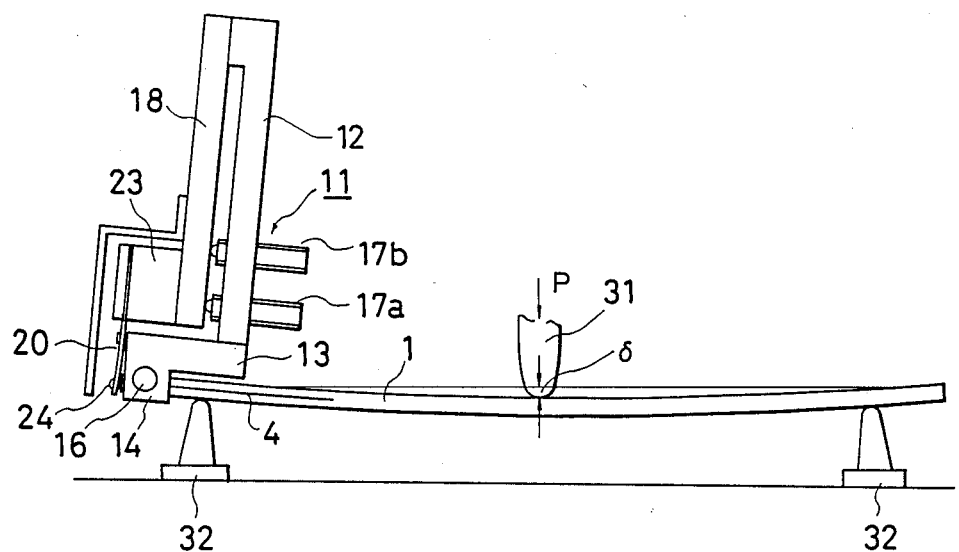
FIG. 5 is an explanatory view showing the state in which measurement of the crack shear displacement of a test specimen is conducted with the gage of the present invention.

After this setup has been completed, the test specimen 1 is rested on supports 32 (FIG. 5) and a load P is applied at the center thereof by an appropriate device 31. As a result, the test specimen 1 bends to give rise to load line displacement δ therein. This causes the lower portion 2b of the test specimen 1 to shift along the crack 4 with respect to the fixed upper portion 2a thereof (chain line in FIG. 3). As the contact 24 follows this shift of the lower portion 2b, the elastic strain of the cantilever 20 is progressively relieved as the contact 24 moves, and the amount of this relief can be read from the strain gage 25. Therefore the crack shear displacement between the end faces 3a and 3b can be accurately determined from the output of the strain gage 25.

Figure 6:
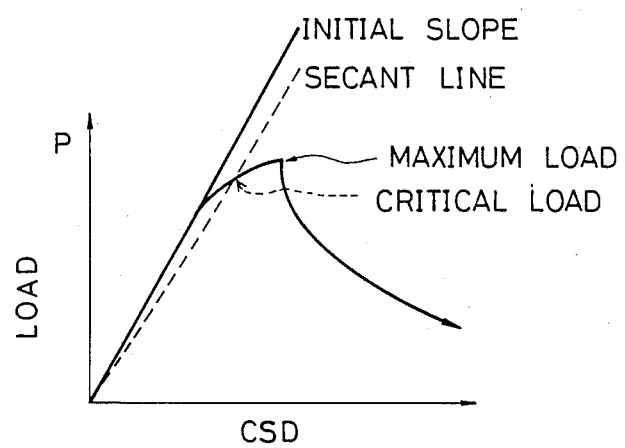
FIG. 6 is a graph showing the relationship between crack shear displacement and critical load.

An example of the relationship between the CSD, as measured in the foregoing manner, and the applied load is shown in FIG. 6. In this case, a secant line is set to have a slope which is 5% smaller than the slope of the initial elastic line portion of the load-CSD curve, the slope of the secant line corresponding to a 2% increase in length of a crack in a notched flexure test specimen.

Since the point of intersection between a load-CSD curve and a secant line is defined as a critical load by the American Society for Testing and Materials (ASTM), when this definition is applied to this example, the point of intersection between the load-CSD curve and the secant line in FIG. 6 can be defined as the critical load (point at which fracture starts). Therefore, the crack shear displacement gage according to this invention enables the critical load to be accurately determined even for a laminate consisting of layers each made of a material high in toughness. Moreover in the gage according to this invention, the bending of the cantilever is greatest at the time the contact is brought against the end face of the test specimen just before the measurement is begun and becomes progressively lower as the load on the test specimen increases. As a result, there is no risk of the gage being damaged or of error being introduced into the measurement even in a case where an excessive applied load causes the test specimen to break.

An example of a measurement conducted with the crack shear displacement gage according to this invention will now be explained. The test specimen used was a laminate consisting of a plurality of composite layers each made of carbon and epoxy, measured 25 mm in width, 140 mm in length and 3 mm in thickness, and had a 45 mm deep crack formed inward from one end face at its center in the thickness direction. The crack shear displacement gage was set up with its head fixed on the end portion of the specimen above the crack and the contact on the cantilever in contact with the end face of the specimen below the crack. The test specimen was then rested on a pair of supports, one of which was about 20 mm apart from the aforementioned one end face of the test specimen and the other one of which was 100 mm apart from the one support, and a gradually increasing load was applied to the center portion of the specimen. The CSD was read and recorded as the load increased.

Figure 7:
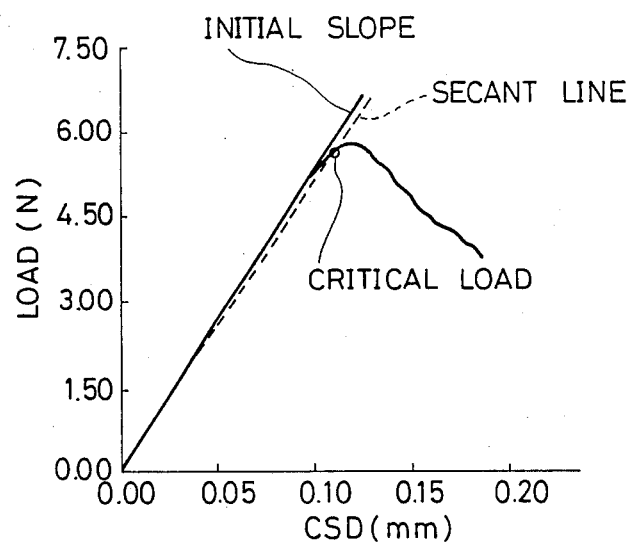
FIG. 7 is an example of a load-CSD curve based on measurements made with a crack shear displacement gage according to this invention.
Figure 8:
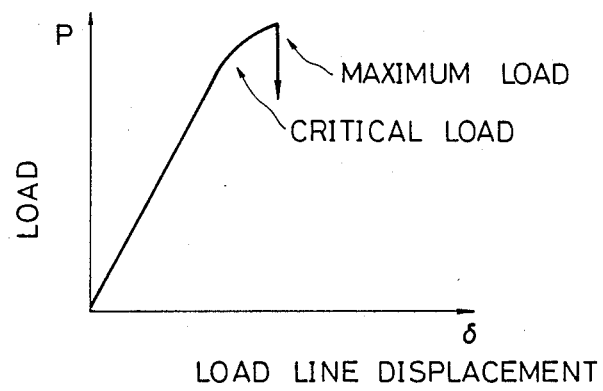
FIG. 8 is a graph showing the conventional relationship between load line displacement and critical load.

The load-CSD curve obtained is shown in FIG. 7. As will be noted, the test specimen exhibited a maximum load of 5.8N, at which time the CSD was about 0.12 mm. From this, the critical load of the laminate was found to be 5.6N.

What is claimed is:

1. A crack shear displacement gage comprising a frame, a fixing member having one end fixed on said frame and having at its other end a fixing head which can be detachably fixed in a clamping manner on a first end portion of a test specimen whose end portion is divided into first and second end portions by a crack, a contact for contacting an end face of said second end portion of said test specimen, a spring member whose one end is fixed on said frame and whose other end supports said contact for urging said contact against said end face of said second end portion, and a strain gage mounted on said spring member for detecting the strain of the spring member.

2. The crack shear displacement gage according to claim 1, further comprising means for adjusting the force of said contact being urged against said end face of said second end portion of said test specimen.

3. The crack shear displacement gage according to claim 1, wherein said fixing head comprises a pair of arms and has means for clamping said first end portion of said test specimen which comprises an internally threaded hole formed in one of said arms, a screw being screwed into said threaded hole and a plurality of projections formed on an inner surface of the other arm.

* * * * *